United States Patent
Takita et al.

(10) Patent No.: US 11,179,469 B2
(45) Date of Patent: Nov. 23, 2021

(54) TRANSDERMAL ABSORPTION PREPARATION

(71) Applicant: Nitto Denko Corporation, Ibaraki (JP)

(72) Inventors: Tomohito Takita, Ibaraki (JP); Kaiji Fujiwara, Ibaraki (JP); Chie Matsumoto, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 0 days.

(21) Appl. No.: 15/935,443

(22) Filed: Mar. 26, 2018

(65) Prior Publication Data

US 2018/0311362 A1    Nov. 1, 2018

(30) Foreign Application Priority Data

Apr. 28, 2017  (JP) .............................. JP2017-090694

(51) Int. Cl.
| | |
|---|---|
| *A61K 47/32* | (2006.01) |
| *A61K 9/70* | (2006.01) |
| *A61K 31/135* | (2006.01) |
| *A61K 31/137* | (2006.01) |

(52) U.S. Cl.
CPC .............. *A61K 47/32* (2013.01); *A61K 9/703* (2013.01); *A61K 9/7053* (2013.01); *A61K 9/7061* (2013.01); *A61K 9/7084* (2013.01); *A61K 31/135* (2013.01); *A61K 31/137* (2013.01)

(58) Field of Classification Search
CPC .. A61K 9/7084; A61K 31/567; A61K 9/0014; A61K 9/7053
See application file for complete search history.

(56) References Cited

U.S. PATENT DOCUMENTS

| | | | |
|---|---|---|---|
| 4,743,249 A * | 5/1988 | Loveland | A61K 9/7084 424/447 |
| 5,614,213 A | 3/1997 | Elger et al. | |
| 5,730,999 A | 3/1998 | Lehmann et al. | |
| 6,063,399 A | 5/2000 | Assmus et al. | |
| 6,117,447 A | 9/2000 | Nakano et al. | |
| 6,461,636 B1 | 10/2002 | Arth et al. | |
| 6,562,367 B1 | 5/2003 | Wolff et al. | |
| 6,899,894 B1 | 5/2005 | Klein et al. | |
| 6,902,741 B1 | 6/2005 | Grawe et al. | |
| 7,056,528 B1 | 6/2006 | Bracht | |
| 2003/0003139 A1 | 1/2003 | Lipp et al. | |
| 2003/0228358 A1* | 12/2003 | Perlman | A61K 9/146 424/465 |
| 2004/0092544 A1 | 5/2004 | Horowski et al. | |
| 2005/0214353 A1 | 9/2005 | Horowski et al. | |
| 2008/0138388 A1 | 6/2008 | Aida et al. | |
| 2008/0226698 A1* | 9/2008 | Tang | A61P 5/26 424/448 |
| 2008/0305155 A1* | 12/2008 | Jackson | A61K 9/7061 424/449 |
| 2009/0136549 A1 | 5/2009 | Lin et al. | |
| 2009/0299304 A1 | 12/2009 | Tang | |
| 2011/0064811 A1 | 3/2011 | Hurter et al. | |
| 2011/0182949 A1* | 7/2011 | Tang | A61K 9/7061 424/400 |
| 2012/0058175 A1* | 3/2012 | Amano | A61K 45/06 424/443 |
| 2013/0216602 A1* | 8/2013 | Clay | A61K 9/0085 424/426 |
| 2013/0220846 A1 | 8/2013 | Hiraoka et al. | |
| 2014/0180201 A1* | 6/2014 | Ding | B29C 43/021 604/46 |
| 2015/0018782 A1* | 1/2015 | Hiraoka | A61K 31/27 604/307 |
| 2016/0193151 A1 | 7/2016 | Noriega Escobar et al. | |
| 2017/0079940 A1 | 3/2017 | Kawakami et al. | |

FOREIGN PATENT DOCUMENTS

| | | | |
|---|---|---|---|
| CN | 1827094 A | | 9/2006 |
| CN | 101674816 A | | 3/2010 |
| CN | 102099020 A | | 6/2011 |
| CN | 102413821 A | | 4/2012 |
| CN | 103919755 A | * | 7/2014 |
| CN | 103919755 A | | 7/2014 |
| CN | 104136025 A | | 11/2014 |
| EP | 0922453 A2 | | 9/2000 |
| EP | 2011488 A1 | | 1/2009 |
| EP | 2425827 A1 | | 3/2012 |
| JP | H06-305953 A | | 11/1994 |
| JP | H07-504672 A | | 5/1995 |

(Continued)

OTHER PUBLICATIONS

PubChem (Rivastigmine, https://pubchem.ncbi.nlm.nih.gov/compound/Rivastigmine, Create date of Aug. 2005 and Modified on Oct. 2019) (Year: 2019).*
Parikh et al (Journal of Excipients and Food Chemicals, Mar. 2014, vol. 5, pp. 56-64) (Year: 2014).*
Fu et al (Oncotarget, 2018, vol. 9, p. 12154-12163) (Year: 2018).*
Chemical Book (Tulobuterol product description, copyright 2017, 41570-61-0) (Year: 2017).*
CN-103919755-A (Espacenet English translation, downloaded in Apr. 2020) (Year: 2020).*
Jadhav et al (Asian Journal of Pharmaceutics, 2009, vol. 3, Glass transition temperatures, pp. 82-89) (Year: 2009).*

(Continued)

*Primary Examiner* — Mark V Stevens (74) *Attorney, Agent, or Firm* — Leydig, Voit & Mayer, Ltd.

(57) ABSTRACT

Provided is a transdermal absorption preparation that shows superior skin permeability of a drug and that does not easily cause cold flow. A transdermal absorption preparation having a drug-containing layer containing a drug and a polymer, wherein 50-100 wt % of the polymer in the drug-containing layer is a polymer having a glass transition temperature of 30° C.-200° C., and the drug in the drug-containing layer is in an amorphous state.

6 Claims, 1 Drawing Sheet

(56) References Cited

FOREIGN PATENT DOCUMENTS

| | | | |
|---|---|---|---|
| JP | H10-182439 A | 7/1998 | |
| JP | 2002-508778 A | 3/2002 | |
| JP | 2002-515424 A | 5/2002 | |
| JP | 2002-518430 A | 6/2002 | |
| JP | 2004-512305 A | 4/2004 | |
| JP | 2004-525872 A | 8/2004 | |
| JP | 2009-522278 A | 6/2009 | |
| JP | 2010-521525 A | 6/2010 | |
| JP | 2011-521974 A | 7/2011 | |
| JP | 2011-252003 A | 12/2011 | |
| JP | 2015-083569 A | 4/2015 | |
| WO | WO 2001/089488 A1 | 11/2001 | |
| WO | WO 2006/082728 A1 | 8/2006 | |
| WO | WO 2009/158120 A2 | 12/2009 | |
| WO | WO 2013/128562 A1 | 6/2013 | |
| WO | WO-2014111790 A2 * | 7/2014 | ........... A61K 9/7053 |
| WO | WO 2015/182459 A1 | 12/2015 | |
| WO | WO 2017/003935 A1 | 1/2017 | |

OTHER PUBLICATIONS

Desai et al., "Development and in Vitro-In Vivo Evaluation of Fenretinide-Loaded Oral Mucoadhesive Patches for Site-Specific Chemoprevention of Oral Cancer," *Pharm. Res.*, 28(10): 2599-2609 (2011).

European Patent Office, Extended European Search Report in European Patent Application No. 18164007.9 (dated Jun. 27, 2018).

Korean Patent Office, Notification of Reason for Refusal in Korean Patent Application No. 10-2018-0034646 (dated Jun. 12, 2019).

Japanese Patent Office, Notice of Reasons for Refusal in Japanese Patent Application No. 2018-058950 (dated May 7, 2019).

Evonik, Eudragit® E PO Copolymer Catalog (2019) [obtained at: http:// http://www.matweb.com/search/datasheet_print.aspx?matguid=43cbe3111b244bfd920f4fc89a08a36d].

Novartis, Package Insert for Exelon® Patch [rivastigmine transdermal system] (Dec. 2018).

Japanese Patent Office, Submission of Publications in Japanese Patent Application No. 2018-188420 (dated Aug. 1, 2019).

Ono Pharamceutical Co., Ltd., Drug Interview Form for Rivastach® Patch, pp. 1-10 (2016).

Japanese Patent Office, Notice of Reasons for Refusal in Japanese Patent Application No. 2018-058950 (dated Jan. 7, 2020).

Kim et al., "Effect of porous silica on sustained release behaviors of pH sensitive Pluronic F127/poly(acrylic acid) hydrogels containing tulobuterol," *Colloids and Surfaces B: Biointerfaces*, 80(2): 240-246 (2010).

European Patent Office, Communication Pursuant to Article 94(3) EPC in European Patent Application No. 18164007.9 (dated Jul. 28, 2020).

China National Intellectual Property Administration, First Office Action in Chinese Patent Application No. 201810252675.3 (dated Nov. 18, 2020).

Luo et al., *Compendium of Pharmaceutical Experiments*, Sichuan Science and Technology Press, 121-123 (Mar. 31, 1993).

China National Intellectual Property Adminstration, The Second Office Action in Chinese Patent Application No. 201810252675.3 (dated Jul. 26, 2021).

* cited by examiner

TRANSDERMAL ABSORPTION PREPARATION

TECHNICAL FIELD OF THE INVENTION

The present invention relates to a transdermal absorption preparation showing promoted skin permeability of drugs.

BACKGROUND OF THE INVENTION

Adhesive preparations including transdermal absorption preparations not only intend to treat lesions on the skin surface or in the tissues directly under skin application site, by topical absorption of the drug, but are also used as preparations expected to act systemically rather than on the skin and nearby tissues by being taken into the blood from subcutaneous blood vessels. They have been recognized as one of the drug delivery systems.

To improve skin permeability of a drug in an adhesive preparation to be adhered to the skin for percutaneous absorption of the drug, the plane area of the adhesive preparation needs to be increased. However, when the flat plane area of the adhesive preparation is large, handling problems (difficult adhesion to the skin etc.) and problems of skin irritation such as stuff, itching sensation and the like after application to the skin occur. When an adhesive preparation is adhered to a different site, problems that a wide adhesion area is difficult to obtain and the like are present. In conventional adhesive preparations, when a permeation promoter is contained in the preparation to improve skin permeability, problems that the cohesion strength of the preparation decreases, cold flow may be developed and the like are present.

Generally, a drug in an amorphous state is known to be superior in the skin permeability to a drug in a crystal state. For example, patent document 1 proposes a transdermal delivery device having an adhesive matrix layer containing a supersaturated concentration of a drug in a substantially amorphous state, and an amorphous form of a drug (active substance) having a high glass transition temperature (Tg) is said to be stabler than an amorphous form of an active substance having a low Tg. Furthermore, it is described that an amorphization promotive backing layer (support) and/or release liner each free of a crystallization nucleus are/is used to avoid crystallization of an amorphous drug.

Patent document 2 proposes a transdermal drug delivery device having an adhesive layer containing an adhesive, an amorphous drug, and a polymeric stabilizing and dispersing agent containing a hydrogen bond forming functional group, and describes that the long-term stability of a drug depends on the ratio of the drug and the polymeric stabilizing and dispersing agent.

However, in the technique described in patent document 1, the stability of the drug in an amorphous state in the preparation depends on the glass transition temperature of the drug, the degree of freedom of the formulation design is not high and the crystal is developed not only from the interface between a support or release liner and an adhesive layer but also from the inside of the adhesive layer. Therefore, mere suppression of the crystal nucleus in the aforementioned interface is not sufficient.

In the technique described in patent document 2, the stability of the drug in an amorphous state in the preparation depends on the ratio of the drug and the polymeric stabilizing and dispersing agent. It is not a technique having a high degree of freedom of the formulation design. In addition, since it is a technique aiming to achieve stabilization by forming a hydrogen bond between the drug and the polymeric stabilizing and dispersing agent, the technique is not applicable to a drug without a functional group capable of forming a hydrogen bond.

DOCUMENT LIST

Patent Documents

[patent document 1] JP-A-2010-521525
[patent document 2] JP-A-2011-521974

SUMMARY OF THE INVENTION

Problems to be Solved by the Invention

Therefore, the present invention aims to provide a transdermal absorption preparation that shows superior skin permeability of a drug and that does not easily cause cold flow.

Means of Solving the Problems

The present inventors have conducted intensive studies in an attempt to solve the above-mentioned problems and found that a transdermal absorption preparation that shows superior skin permeability of a drug and that does not easily cause cold flow can be realized when, in a drug-containing layer containing a drug and a polymer of the transdermal absorption preparation, 50-100 wt % of the polymer is a polymer having a glass. transition temperature of 30° C.-200° C., because an amorphous state of the drug is stably maintained in the drug-containing layer, which resulted in the completion of the present invention.

That is, the present invention relates to the following.
[1] A transdermal absorption preparation comprising a drug-containing layer containing a polymer and a drug, wherein
  the drug in the drug-containing layer is in an amorphous state, and
  50-100 wt % of the aforementioned polymer is a polymer having a glass transition temperature of 30° C.-200° C.
[2] The transdermal absorption preparation of [1] wherein the drug has a melting point of not more than 200° C.
[3] The transdermal absorption preparation of [1] or [2], wherein, in the drug-containing layer containing the drug and the polymer, a ratio of an octanol/water partition coefficient (log P2) of the polymer to an octanol/water partition coefficient (log P1) of the drug (log P2/log P1) is 0.01-1.5.
[4] The transdermal absorption preparation of any of [1] to [3], further comprising a substrate or a cover material, or a substrate and a cover material laminated on the drug-containing layer.
[5] The transdermal absorption preparation of any of [1] to [4], further comprising a skin adhesion layer.
[6] The transdermal absorption preparation of any of [1] to [5] which is in the form of a sheet.

Effect of the Invention

The present invention can provide a transdermal absorption preparation that shows promoted skin permeability of drugs and does not easily cause cold flow.

DESCRIPTION OF EMBODIMENTS

The transdermal absorption preparation of the present invention is a transdermal absorption preparation having a drug-containing layer containing a drug and a polymer, wherein the drug is present in an amorphous state, and 50-100 wt % of the aforementioned polymer is a polymer having a glass transition temperature of 30° C.-200° C.

The "transdermal absorption preparation" in the present invention refers to a preparation used by closely adhering to the skin, and is preferably provided in the form of a sheet, mainly an adhesive preparation such as a tape preparation (e.g., plaster, etc.), cataplasm and the like.

The transdermal absorption preparation of the present invention has a drug-containing layer containing a drug and a polymer, and the drug-containing layer is preferably formed as a plaster layer in a sheet-like adhesive preparation.

In the drug-containing layer containing a drug and a polymer, the drug is present in an amorphous state.

Being "amorphous" here refers to a solid in which, different from crystals, atoms and molecules do not form a regular spatial lattice but are in a disordered arrangement. Whether a drug is in an amorphous state can be judged by whether or not endothermic phenomenon due to melting of the crystal of the drug in the drug containing layer is observed when exothermic and endothermic behavior of the drug during the heating process is evaluated by, for example, Differential scanning calorimetry (DSC).

A drug to be contained in the transdermal absorption preparation of the present invention is not particularly limited, and any can be used as long as it can maintain the amorphous state in the drug-containing layer. Examples thereof include general anesthetic, antipsychotic agent, antidepressant, mood stabilizer, psychostimulant, sleeping drug, antianxiety drug, antiepileptic, therapeutic drug for migrainea, antiemetic, anti-vertiginous drug, local anesthetic, muscle relaxant, autonomic drug, antiepileptic drug, therapeutic drug for Parkinson's disease, anti-dementia drug, adrenal cortical steroid, non-steroidal antiinflammatory agent, analgesic antipyretic drug, therapeutic drug for neuropathic pain, antirheumatic drug, anti-histamine drug, antiallergic agent, cardiotonic drug, antiarrhythmic drug, diuretic, depressor, vasoconstrictor, vasodilator, therapeutic drug for angina pectoris, anapnoic, bronchodilator, therapeutic drug for bronchial asthma, antitussive, expectorant, hormone drug, hematopoietic drug, hemostat, antithrombotic, therapeutic drug for gout-hyperuricemia, therapeutic drug for diabetes, a therapeutic drug for hyperlipidemia, antitumor drug, immunosuppressant, antibiotic, chemotherapy drug, antifungal agent, antiviral drug, antiparasitic agent, narcotic, narcotic analgesics, non-narcotic analgesics, quit-smoking drug and the like. The melting point of the drug is preferably not more than 200° C. and more preferably not more than 100° C. When the drug has a melting point of not more than 200° C., a more superior drug crystallization-suppressive effect can be obtained. The melting point of the drug is preferably not less than 15° C. When the drug has a melting point of not less than 15° C., a permeation promoting effect by the thermodynamic energy developed by amorphization can be obtained.

The melting point of the drug can be measured according to a conventional method. For example, it can be measured according to the method prescribed in the Japanese Pharmacopoeia 17th edition, General Test Method 2.60 Melting Point Measurement Method or the like.

Examples of the drug preferably used in the present invention include antipyretic analgesic drug, therapeutic drug for neuropathic pain, non-narcotic analgesics, narcotic analgesics, antipsychotic agents, anti-dementia drug and the like.

The above-mentioned drugs can be contained in a form suitable for maintaining an amorphous state in the drug-containing layer, such as a free form, form of a salt with an acid or base and the like.

Examples of the salts of the above-mentioned drugs include alkali metal salts such as sodium salt, potassium salt and the like; alkaline earth metal salts such as magnesium salt, calcium salt and the like; inorganic acid salts such as hydrochloride, nitrate, sulfate and the like; organic acid salts such as acetate, octanoate, citrate, fumarate, maleate and the like; salts with inorganic base such as ammonium salt and the like; salts with organic base such as triethanolamine salt, pyridine salt, arginine salt and the like, and the like.

The above-mentioned drug and a salt thereof can be produced according to a production method known per se.

While the content of a drug in the transdermal absorption preparation of the present invention varies depending on the kind of the drug, the age, sex, symptom of patients to whom the transdermal absorption preparation is used, and the like, it is generally 30 wt %-95 wt %, preferably 50 wt %-90 wt %, of the total amount of the drug-containing layer.

In the drug-containing layer, 50-100 wt % of the polymer is a polymer having a glass transition temperature of 30° C.-200° C. A polymer having a glass transition temperature of 30° C.-200° C. is rigid. When not less than 50 wt % of the polymer in the drug-containing layer is a polymer having a glass transition temperature of 30° C.-200° C., the polymer suppresses movement and coagulation of the drug in the drug-containing layer, and suppresses crystallization of the drug present in an amorphous state. Preferably 60-100 wt %, more preferably 70-100 wt %, furthermore preferably 80-100 wt %, particularly preferably 90-100 wt %, most preferably 100 wt %, of the polymer in the drug-containing layer is a polymer having a glass transition temperature of 30° C.-200° C.

For the object of the present invention, the polymer having a glass transition temperature of 30° C.-200° C. preferably has a glass transition temperature of 50° C.-200° C., more preferably 60° C.-180° C.

The "glass transition temperature" here means a temperature at which the rigidity and viscosity decrease rapidly and the flowability increases when an amorphous solid is heated. The glass transition temperature of a polymer can be measured by DSC and the like.

Examples of the polymer having a glass transition temperature of 30° C.-200° C. include cellulose derivatives such as hydroxypropylmethylcellulose, hydroxypropylmethylcellulose phthalate, hydroxypropylcellulose, acetyl cellulose and the like; acrylic polymers such as acrylic resin, methacrylic acid-methyl methacrylate copolymer (methacrylic acid copolymer S ("EUDRAGIT (registered trade mark) S100"), methacrylic acid copolymer L ("EUDRAGIT (registered trade mark) L100"), manufactured by Evonik Rohm GmbH), methacrylic acid-ethyl acrylate copolymer (dried methacrylic acid copolymer LD ("EUDRAGIT (registered trade mark) L100-55", manufactured by Evonik Rohm GmbH)), methyl methacrylate-butyl methacrylate-dimethylaminoethyl methacrylate copolymer (aminoalkyl methacrylate copolymer E ("EUDRAGIT (registered trade mark) EPO", manufactured by Evonik Rohm GmbH)), methyl methacrylate-ethyl acrylate-trimethylammonioethyl methacrylate chloride copolymer (ammonioalkyl methacrylate copolymer ("EUDRAGIT (registered trade mark) RSPO", EUDRAGIT RLPO", manufactured by Evonik Rohm GmbH)), ethyl acrylate-methyl methacrylate copolymer (ethyl acrylate-methyl methacrylate copolymer dispersion solution ("EUDRAGIT (registered trade mark) NE30D", manufactured by Evonik Rohm GmbH)) and the like; polyvinylpyrrolidone; vinylpyrrolidone-vinyl acetate copolymer; polycarbonate; cycloolefin copolymer; polyvinyl caprolactam-polyvinyl acetate-polyethylene glycol graft copolymer ("Soluplus") (registered trade mark), manufactured by BASF); polyvinyl alcohol); polyvinyl acetate and the like. One or more kinds thereof can be used. Of these, acrylic polymer, polyvinylpyrrolidone, vinylpyrrolidone.vinyl acetate copolymer, polyvinyl caprolactam.polyvinyl acetate.polyethylene glycol graft copolymer and the like are preferably used, since molding processing is facilitated by the high glass transition temperature and high solubility in organic solvents.

The polymer in the drug-containing layer can contain less than 50 wt % of a polymer other than the polymer having a glass transition temperature of 30° C.-200° C. As such polymer, a polymer having a glass transition temperature of not less than −100° C. and less than 30° C. is preferable and, for example, an adhesive such as acrylic adhesive, silicone adhesive, rubber adhesive and the like can be used. The content of the polymer is preferably not more than 40 wt %, more preferably not more than 30 wt %, furthermore preferably not more than 20 wt %, particularly preferably not more than 10 wt %, most preferably 0 wt %.

For the object of the present invention, a combination of the drug and polymer contained in the drug-containing layer preferably renders a ratio of an octanol/water partition coefficient (log P2) of the polymer to an octanol/water partition coefficient (log P1) of the drug (log P2/log P1) 0.01-1.5, preferably 0.02-1.0. A combination that renders the ratio (log P2/log P1) 0.01-1.5 shows high compatibility of the drug and the polymer and more advantageously acts on the suppression of the crystallization of the drug present in an amorphous state. Here, the base of the aforementioned logarithm is 10.

The octanol/water partition coefficient (log P1) of the drug is preferably 1-5, more preferably 1-4, further preferably 2-3, from the aspect of skin permeability.

The octanol/water partition coefficient is the ratio of the distribution of a certain chemical substance respectively to n-octanol and water (ratio of the concentration in n-octanol phase and aqueous phase). It is used as an index showing hydrophobicity and transferability of the chemical substance, and can be measured by the flask shaking method prescribed in the Economic Development Cooperation Organization (OECD) Test Guideline 107 and the like or calculated using the calculation software ("Cache Workspace (registered trade mark)" manufactured by Fujitsu Limited) etc. and inputting the structural formula of the compound. The octanol/water partition coefficient of the polymer is calculated using the molecule structural formula in a monomer unit.

In the present invention, the drug-containing layer can contain additives widely used for transdermal absorption preparation such as tackifier, crosslinking agent, excipient, antioxidant, preservative and the like as long as the characteristics of the present invention are not impaired.

While the thickness of the drug-containing layer is not particularly limited, it is preferably not less than 0.1 μm, more preferably not less than 1 μm, from the aspect of handling during production. Also, from the aspect of the transdermal absorbability of drug, it is preferably not more than 1,000 μm, more preferably not more than 500 μm.

In the transdermal absorption preparation of the present invention, a substrate or a cover material, or both a substrate and a cover material can be laminated on the drug-containing layer.

The material of the above-mentioned substrate is not particularly limited, and a preferable material is one that does not allow a drug contained in the drug-containing layer to pass through the substrate and get lost from the back face to decrease the content, namely, one constituted of a material impermeable to the drug. Examples thereof include single films of polyester-based resins such as poly(ethylene terephthalate) and the like; polyamide-based resins such as nylon and the like; olefin-based resins such as polyethylene, polypropylene and the like; vinyl-based resins such as ethylene-vinyl acetate copolymer, polyvinyl chloride, polyvinylidene chloride, ionomer resin and the like; acrylic resins such as ethylene-ethyl acrylate copolymer and the like; fluorocarbon resins such as polytetrafluoroethylene and the like; metal foil and the like, and these laminate films and the like.

The thickness of the substrate is generally 10 μm-200 μm, preferably 15 μm-150 μm, more preferably 20 μm-100 μm.

To improve adhesiveness (anchor property) between the substrate and the drug-containing layer, the substrate is preferably a laminate film of a non-porous film made of the above-mentioned material and a porous film, and the porous film and the drug-containing layer are laminated to be adhered to each other.

The aforementioned porous film is not particularly limited as long as the anchor property between the substrate and the drug-containing layer is improved. Examples thereof include paper, woven fabric, non-woven fabric, mechanically perforation-treated film and the like, particularly paper, woven fabric and non-woven fabric are preferable. The thickness of the porous film is preferably 10 μm-100 μm in consideration of the improvement of the anchor property and flexibility of the drug-containing layer. When woven fabric or non-woven fabric is used as a porous film, the amount thereof is preferably set to 3 g/m$^2$-50 g/m$^2$, more preferably 5 g/m$^2$-30 g/m$^2$, to improve anchor property.

The cover material is generally formed to have a larger planar shape than the planar shape of the drug-containing layer. To adhere or closely adhere the drug-containing layer to the skin, the cover material is laminated on the drug-containing layer or on the above-mentioned substrate laminated on the drug-containing layer.

Therefore, the cover material generally has a skin surface adhesive layer formed on the support.

As a support constituting the cover material, a single film of a resin and the like similar to those mentioned above for the substrate, or a laminate film thereof, or these films laminated with woven fabric, non-woven fabric and the like can be used. Of these, one maintaining skin followability, that is, one easily expanding and/or contracting according to the elongation of the skin surface is preferable. For example, single films and laminate films of thermoplastic resins such as poly(ethylene terephthalate), nylon, polyethylene, polypropylene, ethylene-vinyl acetate copolymer, polyvinyl chloride, polyvinylidene chloride, ionomer resin and polytetrafluoroethylene, and these films laminated with woven fabric or non-woven fabric are preferably used.

As a skin surface adhesive layer in the cover material, an adhesive layer can be formed from an adhesive similar to the adhesive contained in the below-mentioned skin adhesion layer, such as acrylic adhesive, rubber adhesive, silicone adhesive, vinyl ether adhesive and the like.

The skin surface adhesive layer can also be formed from a material similar to the so-called hydrocolloid dressing material. Specifically, it can be formed from a mixed dispersion of an elastomer component and a hygroscopic substance.

Examples of the elastomer component include polyisobutene, polyisoprene, acrylic polymer, styrene-isoprene-styrene block copolymer and the like. One or more kinds of these can be used. In addition to these, polybutadiene, styrene-butadiene-styrene block copolymer, natural rubber, silicone polymer using polymethylsiloxane or the like as the main component, polyvinyl ether polymer and the like can be used.

The hygroscopic substance is not particularly limited, and any component can be used as long as it can impart liquid absorbability to the skin surface adhesive layer. Specifically, sodium carboxymethylcellulose, dextrin, pectin, gelatin and the like can be mentioned, and one or more kinds thereof can be used. In addition to these, calcium carboxymethylcellulose, hydroxypropylcellulose, guar gum, locust bean gum, xanthan gum, sodium alginate, calcium alginate, carrageenan, collagen, polyvinylpyrrolidone and the like can also be used.

Furthermore, the skin surface adhesive layer can also be formed from a moistening adhesiveness composition.

Such moistening adhesiveness composition can be formed as a jelly composition containing a film forming agent such as poly(vinyl alcohol) and the like, a thickener such as sodium carboxymethylcellulose, carboxyvinyl polymer and the like, a moisturizer such as propylene glycol, glycerol, sorbitol and the like, or a paste composition further containing a powder such as titanium oxide, kaolin and the like.

The below-mentioned release liner can be laminated on the skin surface adhesive layer of the cover material to protect the surface to be adhered to the skin until use.

In the present invention, moreover, a skin adhesion layer can be further laminated on the drug-containing layer. It is preferable to laminate a skin adhesion layer to improve adhesiveness to the skin when the drug-containing layer has low skin adhesiveness.

As an adhesive used to form a skin adhesion layer, adhesives widely used for transdermal absorption preparations to be adhered to the skin can be used without particular limitation. For example, acrylic adhesives such as acrylic copolymer of 50-99 wt % of alkyl (meth)acrylate having an alkyl group having 4-12 carbon atoms, and 1-50 wt % of a functional group-containing monomer (e.g., carboxyl group-containing monomer such as (meth)acrylic acid, maleic acid, maleic anhydride and the like, hydroxyl group-containing is monomers such as hydroxyethyl (meth)acrylate, hydroxypropyl (meth)acrylate and the like, sulfo group-containing monomers such as styrene sulfonic acid, ally sulfonic acid, sulfopropyl (meth)acrylate and the like, and the like) and the like; styrene-diene-styrene block copolymer (e.g., styrene-isoprene-styrene block copolymer, styrene-butadiene-styrene block copolymer and the like); rubber adhesives such as polyisoprene, polyisobutene, butyl rubber, polybutadiene and the like; silicone adhesives such as silicone rubber, dimethylsiloxane based, diphenylsiloxane based and the like; vinyl ether adhesives such as polyvinyl methyl ether, polyvinyl ethyl ether, polyvinyl isobutyl ether and the like; vinyl ester adhesives such as vinyl acetate-ethylene copolymer and the like; polyester adhesives composed of a carboxylic acid component such as dimethyl terephthalate, dimethyl isophthalate, dimethyl phthalate and the like and a polyhydric alcohol component such as ethylene glycol and the like, and the like: From the aspect of skin adhesiveness, a water-free adhesive is preferable.

The "water-free adhesive" here is not necessarily limited to one completely free of water, and one containing humidity in the air or a slight amount of water derived from the skin and the like is encompassed therein. The "slight amount of water" here is preferably not more than 5 wt %, more preferably not more than 2 wt %, most preferably not more than 1 wt %, as the water content of a laminate of a support and an adhesive layer.

The "water content of a laminate of a support and an adhesive layer" here means a weight ratio of water contained in the laminate of the support and the adhesive layer (water content (weight percentage) relative to the total weight of the laminate of the support and the adhesive layer). When a release liner is present, the release liner is detached and the water content is measured with a Karl Fischer moisture meter by the coulometric titration method. To be specific, for example, a transdermal absorption preparation to be the sample is punched out in a given size under an environment controlled to temperature=23±2° C. and relative humidity=40±5% RH to produce a test piece. Thereafter, when the test piece has a release liner, the release liner is removed and the piece is cast into a water evaporation apparatus. The test piece is heated in the water evaporation apparatus at 140° C., the water moisture generated thereby is introduced into a titration flask using nitrogen as a carrier and the water content (wt %) of the sample is measured by the Karl Fischer coulometric titration method.

The above-mentioned adhesive may be crosslinked as necessary by a physical crosslinking treatment by UV radiation, radiation irradiation (e.g., electron beam irradiation etc.) and the like or a chemical crosslinking treatment using various crosslinking agents.

The skin adhesion layer may contain an oil-soluble additive as long as the characteristics of the present invention are not impaired. Examples thereof include fatty acids such as acetic acid, caprylic acid, pelargonic acid, capric acid, lauric acid, myristic acid, palmitic acid, stearic acid, oleic acid and the like; hydroxyl acids such as glycolic acid, lactic acid, malic acid, tartaric acid, citric acid and the like; keto acids such as levulinic acid and the like; dicarboxylic acids such as fumaric acid, maleic acid and the like; organic bases such as monoethanolamine, diethanolamine, triethanolamine, diisopropanolamine, triisopropanolamine, pyridine, arginine and the like; plant-derived fats and oils such as olive oil, castor oil, coconut oil and the like; plant-derived waxes such as Carnauba wax, rhus succedanea fruit wax and the like; animal-derived fats and oils such as beef tallow, lard and the like; animal-derived waxes such as liquid lanolin, beeswax and the like; organic solvents such as methanol, ethanol, straight chain or branched propanol, straight chain or branched butanol, straight chain or branched pentanol, straight chain or branched hexanol, straight chain or branched heptanol, dimethyldecyl sulfoxide, methyloctyl sulfoxide, dimethyl sulfoxide, dimethylformamide, dimethylacetamide, dimethyllaurylamide, methylpyrrolidone, dodecylpyrrolidone, isosorbitol, N-methyl-2-pyrrolidone and the like; surfactants such as polyoxyethylene hydrogenated castor oil derivative (polyoxyethylene hydrogenated castor oil 40, polyoxyethylene hydrogenated castor oil 50, polyoxyethylene hydrogenated castor oil 60 etc.), sodium polyoxyethylene alkyl ether sulfate, sodium alkylnaphthalenesulfonate, polyoxyethylene oleylamine, sodium polyoxyethylene oleyl ether phosphate, polyoxyl stearate, decaglyceryl laurate, polyoxyethylene sorbitan fatty acid ester (polyoxyethylene sorbitan monolaurate, polyoxyethylene sorbitan monopalmitate, polyoxyethylene sorbitan monostearate, polyoxyethylene sorbitan monooleate etc.), sorbitan fatty acid ester, polyoxyethylene fatty acid ester, polyoxyethylene polyoxypropylene glycol, sucrose fatty acid ester, amine oxide, sodium lauryl sulfate and the like; stabilizers such as tocopherol and the like; plasticizers such as lactate (ethyl lactate, cetyl lactate etc.), diisopropyl adipate, phthalate (dibutyl phthalate etc.), diethyl sebacate, triethyl citrate, benzyl acetate and the like; hydrocarbons such as squalane, squalene, liquid paraffin and the like; fatty acid esters such as ethyl oleate, oleyl oleate, isopropyl palmitate, octyl palmitate, isopropyl myristate, isotridecyl myristate, octyldodecyl myristate, ethyl laurate, hexyl laurate, isostearyl laurate and the like; polyhydric alcohol-fatty acid esters such as glycerol-fatty acid ester, propylene glycol-fatty acid ester and the like; polyhydric alcohols such as glycerol, ethylene glycol, diethylene glycol, propylene glycol, dipropylene glycol, triethylene glycol, 1,3-propanediol, 1,3-butanediol, polyethylene glycol, polypropylene glycol and the like; straight chain aliphatic alcohol such as 1-octanol, 1-dodecanol, 1-tetradecanol, 1-hexadecanol, 1-octadecanol, 1-eicosanol, 1-docosanol, oleyl alcohol, cetostearyl alcohol and the like; branched chain aliphatic alcohols such as 2-hexyl-1-decanol, 2-hexyl-1-dodecanol, 2-octyl-1-dodecanol, 2-hexyl-1-tetradecanol, lanolin alcohol, isostearyl alcohol and the like, cholesterol, phytosterol, ethoxylated stearyl alcohol, hydrogenated rapeseed oil alcohol, α-olefin oligomer, silicone oil and the like. One kind of these additives may be used alone or two or more kinds thereof may be used in combination.

The skin adhesion layer can also contain, for example, tackifiers such as rosin resin, polyterpene resin, coumarone-indene resin, petroleum resin, terpene-phenol resin, xylene resin and the like, as long as the characteristics of the present invention are not impaired.

When the transdermal absorption preparation of the present invention is a transdermal absorption preparation having a skin adhesion layer laminated on the drug-containing layer, it is preferable to separately preserve the drug-containing layer and the skin adhesion layer until the transdermal absorption preparation is adhered to the skin surface, and the skin adhesion layer is laminated on the drug-containing layer and used when the transdermal absorption preparation is adhered to the skin surface.

A release liner may be laminated on the adhesive face to protect an adhesive face of the drug-containing layer or skin adhesion layer during preservation of the transdermal absorption preparation.

While the above-mentioned release liner is not particularly limited, glassine, polyethylene, polypropylene, polyester (e.g., poly(ethylene terephthalate) etc.), polystyrene, aluminum film, foamed polyethylene film or foamed polypropylene film and the like, or a laminate of those selected therefrom, or those further subjected to silicone processing or emboss processing and the like.

The thickness of the release liner is generally 10 μm-200 μm, preferably 25 μm-100 μm.

Of the above-mentioned release liners, those composed of a polyester (particularly, poly(ethylene terephthalate)) resin is preferable from the aspects of barrier property and cost. In this case, those having a thickness of about 25 μm-100 μm are more preferable from the aspect of handling property.

As the release liner, one having an interface side with the drug-containing layer or skin adhesion layer subjected to an easy release treatment is preferable to facilitate detachment of the drug-containing layer or the skin adhesion layer.

The easy release treatment can be performed using a known method. For example, a treatment to form an easy release-treated layer by using a mold release agent containing a curable silicone resin as a main component by a coating method such as bar coating, gravure coating and the like can be mentioned.

The thickness of the easy release-treated layer is preferably 0.01 μm-5 μm to ensure release property and uniformity of the coated film. The thickness of the release liner having an easy release-treated layer is generally 10 μm-200 μm, preferably 25 μm-100 μm, from the aspect of handling property.

The release liner having a laminate (cover) of a drug-containing layer or a skin adhesion layer preferably has an extended part protruding from the periphery of the drug-containing layer or the skin adhesion layer. The length of the extended part (length protruding from the periphery of the drug-containing layer or skin adhesion layer) is preferably about 0.5 mm-10 mm, more preferably about 1 mm-3 mm.

It is preferable to form a sheet of the transdermal absorption preparation of the present invention and provide same as a transdermal absorption preparation sheet (hereinafter to be also referred to as the "transdermal absorption drug sheet" in the present specification).

The transdermal absorption drug sheet of the present invention may be provided as a tape preparation (e.g., plaster, etc.), cataplasm and the like.

The transdermal absorption preparation of the present invention contains, during production, a drug in an amorphous state in the drug-containing layer. For example, it can be produced by dissolving a polymer including a polymer having a glass transition temperature of 30° C.-200° C. and a drug in a suitable organic solvent capable of dissolving them, applying the obtained solution on a release liner and drying same to form a drug-containing layer and, where necessary, laminating a substrate or a cover material on the drug-containing layer. When a substrate or a cover material is laminated on the drug-containing layer, the aforementioned solution of the drug and polymer may be directly applied on the substrate or cover material and dried to form a drug-containing layer on the substrate or cover material.

When the drug and the polymer including a polymer having a glass transition temperature of 30° C.-200° C. shows a ratio of octanol/water partition coefficient thereof (log P2/log P1) within the above-mentioned range of 0.01-1.5, and the drug and the aforementioned polymer have high compatibility, they are kneaded with heating using a biaxial hot melt extruder and the like to prepare a molten mixture of the drug and the polymer, an appropriate amount of the molten mixture is placed on the release liner or a substrate or a cover material and compression molded using a heat pressing machine, whereby a drug-containing layer can also be formed. Alternatively, the above-mentioned molten mixture may be formed using a T-die into a sheet on a release liner to form a drug-containing layer.

In the case of a transdermal absorption preparation further having a skin adhesion layer, the constituent components of a skin adhesion layer such as an adhesive, a tackifier and the like are added to and dissolved in an organic solvent such as methanol, ethyl acetate, toluene and the like to prepare a coating solution, the coating solution is applied on a release liner and dried to form a skin adhesion layer, and a drug-containing layer may be laminated on a surface opposite from the release liner of the skin adhesion layer.

In the case of a transdermal absorption preparation having a skin adhesion layer, it can be provided in an embodiment in which a drug-containing layer and the skin adhesion layer are separately prepared, preserved in a separated state, and they are laminated immediately before adhesion to the skin.

For example, a drug-containing layer and a skin adhesion layer are formed at a distance on one sheet of a release liner or a substrate or a cover material by the above-mentioned method, each is protected with a release liner and the like, packaged with a packaging material and preserved.

In the embodiment in which a drug-containing layer and the skin adhesion layer are separately prepared, preserved in a separated state, and they are laminated immediately before adhesion to the skin, a package containing, together with the drug-containing layer and the skin adhesion layer, a written matter describing that the drug-containing layer and the skin adhesion layer should be laminated and adhered to the skin when the transdermal absorption preparation is used may be provided.

EXAMPLES

The present invention is explained in detail by the Examples. In the following, "part" means "part by weight" unless particularly indicated.

The drug and polymer used for the preparation of the transdermal absorption drug sheets of the Examples and Comparative Examples are as follows.
(1) Tulobuterol: melting point=90° C., log P1=2.55
(2) Tramadol octanoate: prepared from Tramadol hydrochloride by the method shown below. melting point=61° C., log P1=2.37
<Preparation Method>
Tramadol hydrochloride and sodium octanoate were dissolved in ultrapure water at equimolar amounts, ethyl acetate was further added and the mixture was stirred. Using a separatory funnel, the ethyl acetate layer was collected and washed with ultrapure water. Ethyl acetate was removed with an evaporator from the ethyl acetate layer after washing, methanol was further added and the solvent was removed. The residue after solvent removal was dried with a vacuum pump for about 16 hr to give a crystal of tramadol octanoate.
(3) pregabalin: melting point=201° C., log P1=0.89
(4) vinylpyrrolidone.vinyl acetate copolymer: "Kollidon VA64" (manufactured by BASF), glass transition temperature=101° C., log P2=0.30
(5) methacrylic acid.methyl methacrylate copolymer: "Eudragit L100" (manufactured by Evonik Rohm), glass transition temperature=150° C., log P2=0.88
(6) methyl methacrylate.ethyl acrylate.trimethylammonioethyl methacrylate chloride copolymer: "Eudragit RSPO" (manufactured by Evonik Rohm), glass transition temperature=65° C., log P2=0.90
(7) acrylic acid.2-ethylhexyl acrylate copolymer (acrylic copolymer): prepared by the method shown below. glass transition temperature=−65.4° C., log P2=3.27
<Preparation Method>
Under an inert gas atmosphere, 2-ethylhexyl acrylate (95 parts), acrylic acid (5 parts) and azobisisobutyronitrile (0.2 part) were subjected to solution polymerization in ethyl acetate at 60° C. to give an ethyl acetate solution of the above-mentioned copolymer.
(8) polyisobutene: prepared by the method shown below. glass transition temperature=−71° C., log P2=1.63
<Preparation Method>
polyisobutene ("Oppanol B80" (manufactured by BASF), viscosity average molecular weight=800,000) (28.5 parts), polyisobutene ("Himol 6H" (manufactured by JX Energy), viscosity average molecular weight=60,000) (43 parts), polybutene ("Nisseki Polybutene HV-300F" (manufactured by JX Energy), viscosity average molecular weight=1,400) (8.5 parts), and alicyclic saturated hydrocarbon resin ("Alcon P-100" (manufactured by Arakawa Chemical Industries, Ltd.)) (20 parts) were dissolved in hexane to prepare a hexane solution of polyisobutene.
(9) polycarbonate: glass transition temperature=153° C., log P2=4.39

[Example 1] Transdermal Absorption Drug Sheet

A vinylpyrrolidone.vinyl acetate copolymer (70 parts) and Tulobuterol (30 parts) were added to an appropriate amount of methanol, and the mixture was uniformly dissolved by sufficiently mixing and stirring to give a coating solution. The obtained coating solution was applied to a release-treated surface of a poly(ethylene terephthalate) release liner (thickness=75 μm, hereinafter sometimes to be referred to as "PET liner") release-treated with a silicone release agent to a thickness after drying of about 30 μm and dried to form a drug-containing layer. Then, a poly(ethylene terephthalate) film (thickness=25 μm, hereinafter sometimes to be referred to as "PET film") was adhered to a surface opposite from the PET liner of the drug-containing layer to give the transdermal absorption drug sheet of Example 1.

[Comparative Example 1] Transdermal Absorption Drug Sheet

In the same manner as in Example 1 except that a hexane solution of polyisobutene (70 parts as a solid content) was used instead of the vinylpyrrolidone.vinyl acetate copolymer and hexane was used instead of methanol as an organic solvent, a transdermal absorption drug sheet was obtained.

[Comparative Example 2] Transdermal Absorption Drug Sheet

Polycarbonate (70 parts) and Tulobuterol (30 parts) were kneaded with heating and extruded by a biaxial hot melt extruder to give a mixture. An appropriate amount of the above-mentioned mixture was placed on a release-treated surface of a PET liner (thickness=75 μm), covered with a PET film (thickness=25 μm), and compression molded with a heat press into a sheet with a mixture thickness of 30 μm to give a transdermal absorption drug sheet.

However, in the prepared transdermal absorption drug sheet, polycarbonate and Tulobuterol were completely separated by visually observation, and the sheet could not be subjected to the following evaluation.

[Example 2] Transdermal Absorption Drug Sheet

Methacrylic acid-methyl methacrylate copolymer (20 parts) and tramadol octanoate (80 parts) were kneaded with heating and extruded by a biaxial hot melt extruder to give a mixture. An appropriate amount of the above-mentioned mixture was placed on a release-treated surface of a PET liner (thickness=75 μm), covered with a PET film (thickness=25 μm), and compression molded with a heat press into a sheet with a mixture thickness of 250 μm to give a drug-containing layer.

On the other hand, an ethyl acetate solution of acrylic copolymer as an acrylic adhesive (34.7 parts as a solid content), isopropyl myristate (65 parts) and trifunctional isocyanate ("CORONATE HL" (manufactured by Nippon Polyurethane Industry Co., Ltd.) (0.3 part as a solid content) as a crosslinking agent were added to an appropriate amount of ethyl acetate. The mixture was uniformly dissolved by sufficient mixing and stirring to give a coating solution. The obtained coating solution was applied to a release-treated surface of PET liner (thickness=75 μm) to a thickness after drying of about 100 μm and dried to form a skin adhesion layer.

Then, a surface of the drug-containing layer prepared earlier from which the PET liner had been detached was adhered to a surface opposite from the PET liner of the above-mentioned skin adhesion layer, they were stood at 23° C. for 2 hr to give the transdermal absorption drug sheet of Example 2.

[Comparative Example 3] Transdermal Absorption Drug Sheet

In the same manner as in Example 2 except that the sheet was stood at 23° C. for 2 days, the transdermal absorption drug sheet of Comparative Example 3 was obtained.

[Comparative Example 4] Transdermal Absorption Drug Sheet

A methyl methacrylate.ethyl acrylate. trimethylammonioethyl methacrylate chloride copolymer (60 parts) and pregabalin (40 parts) were kneaded with heating and extruded by a biaxial hot melt extruder to give a mixture. An appropriate amount of the aforementioned mixture was placed on a release-treated surface of a PET liner (thickness=75 μm), further covered with a PET film (thickness=25 μm), and compression molded with a heat press into a sheet with a mixture thickness of 100 μm to give a transdermal absorption drug sheet.

The respective transdermal absorption drug sheets of the Examples and Comparative Examples were subjected to the following evaluation.

(1) Drug State

One day after preparation of each transdermal absorption drug sheet, about 5 mg of each drug-containing layer or a laminate of a drug-containing layer and a skin adhesion layer was collected, and the temperature was raised from −20° C. to a temperature 30° C. higher than the melting point of the drug at 3° C./rain and measured by a differential scanning calorimeter ("Q2000" (manufactured by TA Instruments)). In the obtained DSC curve (curve plotting heat flow in the vertical axis and temperature in the horizontal axis), when an endothermic peak was observed near the melting point of the drug, the drug was judged to be in a crystal state and when an endothermic peak was not observed, the drug was judged to be in an amorphous state.

(2) Measurement of Skin Permeation Amount of Drug

One day after preparation of each transdermal absorption drug sheet, a transdermal absorption type drug sheet was adhered to a stratum corneum layer surface of the skin (intact skin) isolated from the abdomen of a hairless mouse, a receptor solution was sampled at every given time by using a flow through diffusion cell apparatus, and the skin permeation amount 24 hr later was calculated. As the receptor solution, phosphate buffered saline at 32° C. was used and the flow was set to about 2.5 mL/h. The concentration of the drug in the receptor solution was quantified using "ACQUITY UPLC" (manufactured by Waters) by ultra high performance liquid chromatography (UPLC) according to "Systemic screening protocol to improve development efficiency of analysis method", M. Maziarz, S. M. McCarthy and M. Wrona, Waters Corporation and the like for Tulobuterol and Tramadol octanoate. For pregabalin, it was quantified using "ACQUITY TQD" (manufactured by Waters) by liquid chromatography-tandem mass spectrometry method (LCMSMS) according to "Validation of Pregabalin in Human Plasma by LCMS Method", G. Uma, M. Manimala, M. Vasudevan, S. Karpagam and Deecaraman; International Journal of Research and Development in Pharmacy and Life sciences, 2012, Vol. 1, No. 3, 151-155 and the like.

(3) Cohesive Property

One day after formation of a drug-containing layer of a transdermal absorption drug sheet, thumb was pressed against each drug-containing layer for about 3 seconds, the finger was peeled off from the drug-containing layer, the presence or absence of attachment on the finger was observed, and the cohesive property of the drug-containing layer was evaluated according to the following evaluation criteria.

<Evaluation Criteria>

○: no attachment on the finger and cohesive property is good

Figure 1:
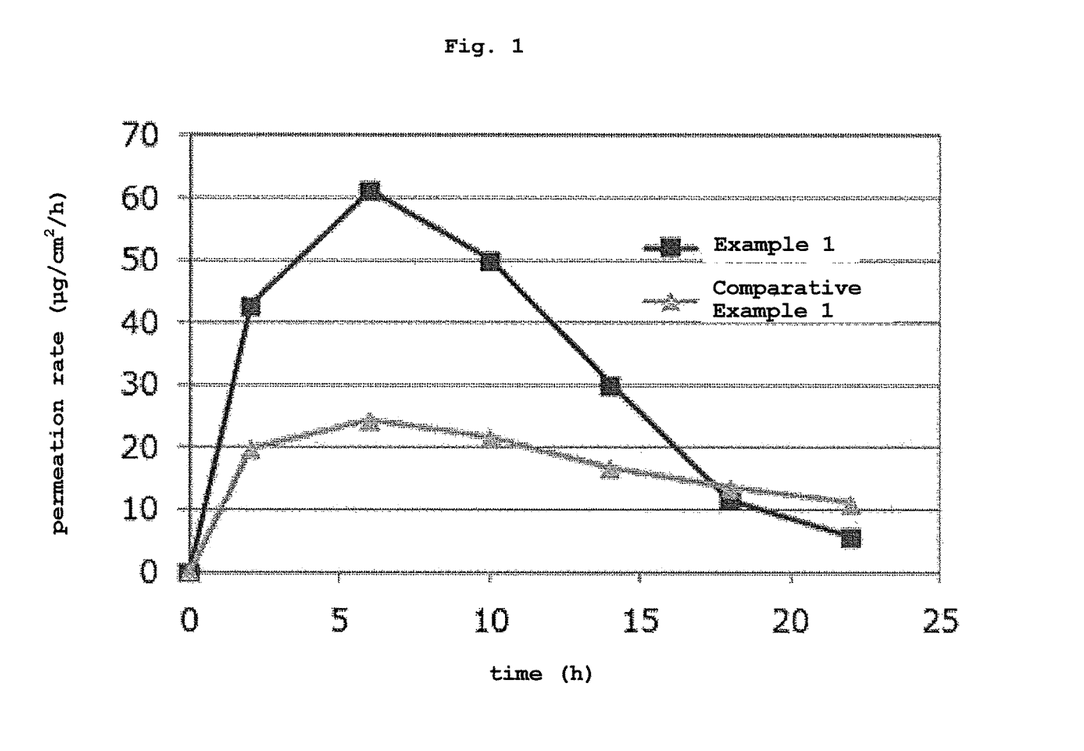
FIG. 1 shows skin permeation rates of drugs in the transdermal absorption type drug sheets of Example 1 and Comparative Example 1 by the evaluation of skin permeability of drug using the abdominal skin of hairless mice.

Δ: slight attachment on the finger, less than 10% of the drug-containing layer is detached from PET film, and the cohesive property is rather bad x: marked attachment on the finger, not less than 10% of the drug-containing layer is detached from PET film, and the cohesive property is bad The evaluation results of the transdermal absorption drug sheets of Example 1 and Comparative Examples 1, 2 are shown in Table 1 together with the properties of the drug and the polymer forming the drug-containing layer. The skin permeation rates of the drug in the transdermal absorption drug sheets of Example 1 and Comparative Example 1 are shown in FIG. 1.

TABLE 1

| transdermal absorption drug sheet | constituent components of drug-containing layer | | drug | | polymer | | | evaluation results | | |
|---|---|---|---|---|---|---|---|---|---|---|
| | drug | polymer | melting point (° C.) | logP1 | Tg (° C.) | logP2 | logP2/logP1 | drug state | skin permeation amount (μg/cm$^2$/24 h) | cohesive property |
| Example 1 | Tulobuterol | vinylpyrrolidone•vinyl acetate copolymer | 90 | 2.55 | 101 | 0.3 | 0.1 | amorphous | 806 | ○ |

TABLE 1-continued

| transdermal absorption drug sheet | constituent components of drug-containing layer | | drug melting point (° C.) | logP1 | polymer Tg (° C.) | logP2 | logP2/ logP1 | evaluation results drug state | skin permeation amount (μg/cm²/24 h) | cohesive property |
|---|---|---|---|---|---|---|---|---|---|---|
| | drug | polymer | | | | | | | | |
| Comparative Example 1 | Tulobuterol | polyisobutene | 90 | 2.55 | −71 | 1.63 | 0.6 | crystal | 429 | Δ |
| Comparative Example 2 | Tulobuterol | polycarbonate | 90 | 2.55 | 153 | 4.39 | 1.7 | evaluation not possible due to separation of drug and polymer | | |

As shown in Table 1 and FIG. 1, the drug was present in an amorphous state in the drug-containing layer of the transdermal absorption drug sheet of Example 1 of the present invention, and sufficient and rapid skin permeation of the drug was obtained. The cohesive property of the drug-containing layer was good.

In contrast, in the transdermal absorption drug sheet of Comparative Example 1 in which the glass transition temperature (Tg) of the polymer constituting the drug-containing layer was −71° C., the drug was present in a crystal state in the drug-containing layer, and sufficient and rapid skin permeation of the drug was not found. In addition, the cohesive property of the drug-containing layer was evaluated as rather bad.

The transdermal absorption drug sheet of Comparative Example 2 in which the drug and polymer contained in the drug-containing layer show a ratio of an octanol/water partition coefficient (log P2) of the polymer to an octanol/water partition coefficient (log P1) of the drug (log P2/log P1) of 1.7 showed separation of the drug and the polymer in the drug-containing layer, and a stable transdermal absorption preparation was not obtained.

The properties of the drug and the polymer forming the drug-containing layer and the property of the adhesive forming the skin adhesion layer of the transdermal absorption drug sheets of Example 2 and Comparative Example 3 are shown in Table 2, and the evaluation results are shown in Table 3. In addition, the skin permeation rates of the drug in the transdermal absorption drug sheets of Example 2 and Comparative Example 3 are shown in FIG. 2.

TABLE 3

| transdermal absorption drug sheet | standing time (time) | drug state | evaluation results skin permeation amount (μg/cm²/24 h) | cohesive property |
|---|---|---|---|---|
| Example 2 | 2 | amorphous | 6941 | ○ |
| Comparative Example 3 | 48 | crystal | 5580 | ○ |

Figure 2:
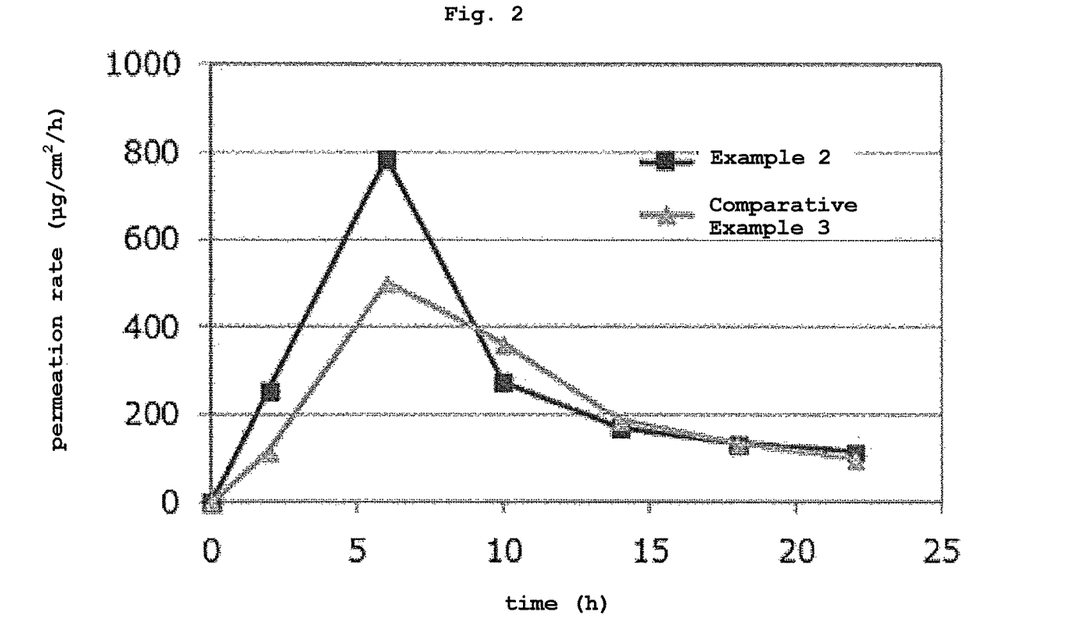
FIG. 2 shows skin permeation rates of drugs in the transdermal absorption type drug sheets of Example 2 and Comparative Example 3 by the evaluation of skin permeability of drug using the abdominal skin of hairless mice.

As shown in Table 3 and FIG. 2, in the transdermal absorption drug sheet of Example 2 in which the skin adhesion layer was laminated on the drug-containing layer and stood for 2 hr, the drug was present in an amorphous state in the laminate of the drug-containing layer and the skin adhesion layer, and good and rapid skin permeation of the drug was found.

In contrast, in the transdermal absorption drug sheet of Comparative Example 3 in which the skin adhesion layer was laminated on the drug-containing layer and stood for 48 hr, the drug was present in a crystal state in the laminate of the drug-containing layer and the skin adhesion layer, and the skin permeation of the drug was found to a certain degree but not sufficient.

The evaluation results of the transdermal absorption drug sheet of Comparative Example 4 are shown in Table 4 together with the properties of the drug and the polymer forming the drug-containing layer.

TABLE 2

| constituent components of drug-containing layer | | drug melting point (° C.) | logP1 | polymer Tg (° C.) | logP2$_a$ | logP2$_a$/ logP1 | skin adhesion layer an adhesive/ oil-soluble additive | adhesive Tg (° C.) | logP2$_b$ | logP2$_b$/ logP1 |
|---|---|---|---|---|---|---|---|---|---|---|
| drug | polymer | | | | | | | | | |
| Tramadol octanoate | methacrylic acid•methyl methacrylate copolymer | 61 | 2.37 | 150 | 0.88 | 0.4 | acrylic copolymer/ isopropyl myristate | −65.4 | 3.27 | 1.4 |

TABLE 4

| transdermal absorption drug sheet | constituent components of drug-containing layer | | drug | | polymer | | logP2/ logP1 | drug state | skin permeation amount (μg/cm²/24 h) | cohesive property |
|---|---|---|---|---|---|---|---|---|---|---|
| | drug | polymer | melting point (° C.) | logP1 | Tg (° C.) | logP2 | | | | |
| Comparative Example 4 | pregabalin | methyl methacrylate•ethyl acrylate•trimethyl-ammonioethyl methacrylate chloride copolymer | 201 | 0.89 | 65 | 0.9 | 1 | crystal | 6 | ○ |

As shown in Table 4, in the transdermal absorption drug sheet of Comparative Example 4 containing pregabalin having a melting point of 201° C., the drug was present in a crystal state in the drug-containing layer, and sufficient skin permeation of the drug was not found.

INDUSTRIAL APPLICABILITY

As described in detail above, the present invention can provide a transdermal absorption preparation that excellently improves skin permeability of a drug, shows no decrease in the cohesive property and suppresses cold flow.

The transdermal absorption preparation of the present invention can be preferably provided as a sheet preparation.

This application is based on a patent application No. 2017-090694 filed in Japan, the contents of which are incorporated in full herein.

The invention claimed is:

1. A transdermal absorption preparation comprising (a) a drug-containing layer, (b) a skin adhesion layer, (c) a substrate, a cover material, or both a substrate and a cover material, and (d) a release liner,
   wherein
   the drug-containing layer comprises a polymer and a drug in an amorphous state,
   50-100 wt % of the polymer is a polymer having a glass transition temperature of 30° C.-200° C. and the drug has a melting point from 15° C.-200° C.,
   wherein the drug-containing layer has a ratio of an octanol/water partition coefficient (logP2) of the polymer to an octanol/water partition coefficient (logP1) of the drug (logP2/logP1) of 0.01-1.5,
   the drug-containing layer and the skin adhesion layer are configured to be separately preserved until the transdermal absorption preparation is adhered to a skin surface,
   whereupon the drug-containing layer laminated onto the skin adhesion layer in contact with the skin surface provides for transdermal absorption of the drug, and
   the substrate, the cover material, or both the substrate and the cover material are laminated on the drug-containing layer, and
   the drug-containing layer and the skin adhesion layer are formed at a distance on one sheet of the release liner, the substrate, or the cover material.

2. The transdermal absorption preparation according to claim 1, which is in the form of a sheet.

3. The transdermal adsorption preparation according to claim 1, wherein the polymer having a glass transition temperature of 30° C.-200° C. is at least one polymer selected from the group consisting of acrylic polymer, polyvinylpyrrolidone, vinylpyrrolidone • vinyl acetate copolymer, and polyvinyl caprolactam • polyvinyl acetate • polyethylene glycol graft copolymer.

4. The transdermal absorption preparation according to claim 1, wherein the drug has a melting point from 15° C.-100° C.

5. The transdermal absorption preparation according to claim 2, wherein the polymer having a glass transition temperature of 30° C.-200° C. is at least one polymer selected from the group consisting of acrylic polymer, polyvinylpyrrolidone, vinylpyrrolidone • vinyl acetate copolymer, and polyvinyl caprolactam • polyvinyl acetate • polyethylene glycol graft copolymer.

6. The transdermal absorption preparation according to claim 5, wherein the drug has a melting point from 15° C.-100° C.

* * * * *